United States Patent
Lee et al.

(10) Patent No.: US 10,366,783 B2
(45) Date of Patent: Jul. 30, 2019

(54) IMAGING EXAMINATION PROTOCOL UPDATE RECOMMENDER

(71) Applicant: KONINKLIJKE PHILIPS N.V., Eindhoven (NL)

(72) Inventors: Michael Chun-chieh Lee, Lexington, MA (US); Eric Cohen-Solal, Ossining, NY (US); Julien Senegas, Hamburg (DE); Stefanie Remmele, Landshut (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1135 days.

(21) Appl. No.: 14/369,791

(22) PCT Filed: Dec. 19, 2012

(86) PCT No.: PCT/IB2012/057468
§ 371 (c)(1),
(2) Date: Jun. 30, 2014

(87) PCT Pub. No.: WO2013/098721
PCT Pub. Date: Jul. 4, 2013

(65) Prior Publication Data
US 2014/0365244 A1    Dec. 11, 2014

Related U.S. Application Data

(60) Provisional application No. 61/581,667, filed on Dec. 30, 2011.

(51) Int. Cl.
*G16H 10/60* (2018.01)
*G06F 19/00* (2018.01)
*G16H 30/00* (2018.01)

(52) U.S. Cl.
CPC .......... *G16H 10/60* (2018.01); *G06F 19/321* (2013.01); *G16H 30/00* (2018.01); *F04C 2270/041* (2013.01)

(58) Field of Classification Search
CPC .............................. G06Q 50/22; G06Q 50/24
See application file for complete search history.

(56) References Cited

U.S. PATENT DOCUMENTS

| 6,674,449 B1 * | 1/2004 | Banks | A61B 5/055 715/740 |
|---|---|---|---|
| 8,195,476 B2 | 6/2012 | Fuchs et al. | |
| 2004/0020698 A1 | 2/2004 | Gehrke et al. | |
| 2004/0082845 A1 * | 4/2004 | Matsumoto | A61B 6/00 600/407 |

(Continued)

FOREIGN PATENT DOCUMENTS

| JP | 2010201002 A | 9/2010 |
|---|---|---|
| JP | 2010237800 A | 10/2010 |

*Primary Examiner* — Linh Giang Le

(57) ABSTRACT

A computing device (126) includes a recommender (134) that evaluates at least one of a user interaction with a displayed image of a scan of an imaging examination protocol or information about the scan in an electronically formatted radiology report, and generates a signal including a recommendation to remove the scan only in response to at least one of the user interaction or the radiology report information satisfying predetermined criteria and a output device (140) that visually presents the signal, thereby visually presenting the recommendation.

18 Claims, 2 Drawing Sheets

(56) References Cited

U.S. PATENT DOCUMENTS

Figure 1:
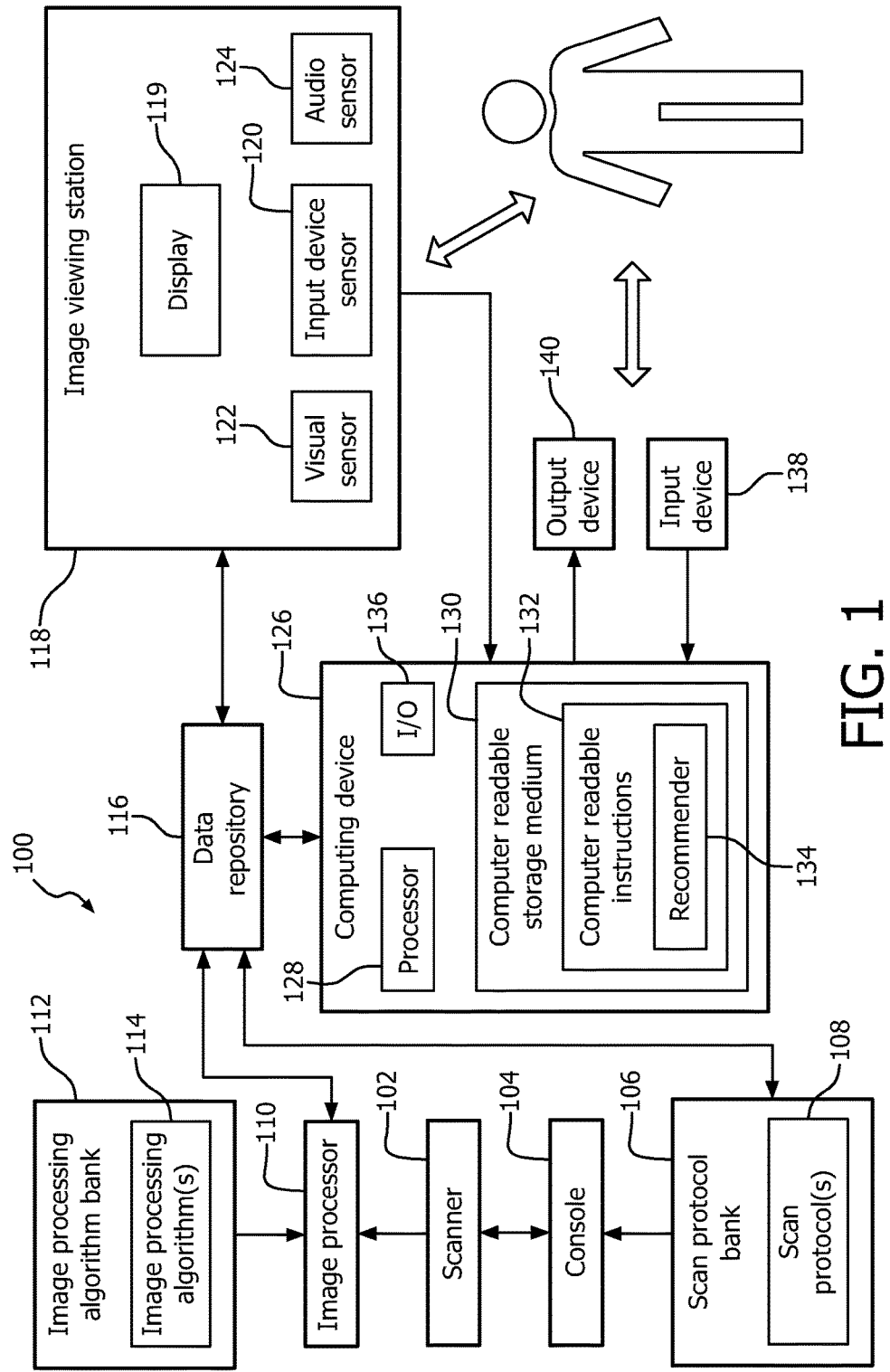

| | | |
|---|---|---|
| 2007/0179811 A1 | 8/2007 | Reiner |
| 2007/0232868 A1* | 10/2007 | Reiner .................. G06F 19/321 |
| | | 600/300 |
| 2009/0006131 A1 | 1/2009 | Unger et al. |
| 2009/0006132 A1* | 1/2009 | Avinash ................. G06Q 50/24 |
| | | 705/3 |
| 2009/0018867 A1* | 1/2009 | Reiner ................ G06F 3/04883 |
| | | 705/2 |
| 2009/0030303 A1* | 1/2009 | Pradeep ................ G06Q 30/00 |
| | | 600/411 |
| 2010/0138230 A1* | 6/2010 | Van Hoe ............... G06F 19/321 |
| | | 705/2 |
| 2011/0046979 A1 | 2/2011 | Tulipano et al. |
| 2011/0116716 A1* | 5/2011 | Kwon .................... G06K 9/036 |
| | | 382/199 |
| 2013/0173308 A1* | 7/2013 | Hough ............. G06F 17/30265 |
| | | 705/3 |

* cited by examiner

IMAGING EXAMINATION PROTOCOL UPDATE RECOMMENDER

This application is a national stage application under 35 U.S.C. § 371 of International Application No. PCT/IB2012/057468 filed on Dec. 19, 2012 and published in the English language on Jul. 4, 2013 as International Publication No. WO/2013/098721, which claims priority to U.S. Application No. 61/581,667 filed on Dec. 30, 2011, the entire disclosures of which are incorporated herein by reference.

The following generally relates to imaging and more particularly to an apparatus and/or method that generates a signal that includes a recommended update to an imaging examination protocol which results in the imaging examination protocol including scans satisfying criteria that are based on radiologist interaction with images generated from performed scans of patients, of patient studies corresponding to the imaging examination protocol, radiology reports corresponding to such scans, other imaging examination protocols, and/or predetermined exceptions.

In clinical practice, an imaging examination protocol often includes multiple individual scans. These scans typically employ different imaging parameters and/or reconstructions, and show different types of anatomies and/or different properties or appearances of pathologies. By way of non-limiting example, a single imaging examination protocol may include several individual and different magnetic resonance imaging (MRI) pulse sequences or scans that result in several different acquired image volumes. For one of the scans, the corresponding image volume may be based on T1-weighting, whereas for another one of the scans, the corresponding image volume may be based on T2-weighting.

The same or other single imaging examination protocol may also include MRI and/or computed tomography (CT) contrast enhanced scans, which require administration of a contrast agent for the scan, and a non-contrast enhanced scans in which no contrast agent is administered to the patient for the scan. The different scans may also include different image processing approaches. For example, in CT, different reconstructions and/or projection images can be produced from the data acquired for the same single acquisition. In MR, acquired data, such as that acquired via diffusion imaging, can be processed to create one or more different image volumes. In x-ray imaging, multiple views (e.g., oblique, A-P, P-A, L-R, R-L and the like) may be obtained from the same patient.

Each of the scans in an imaging examination protocol consumes patient, technologist and/or radiologist time, adds cost, and, in the case of CT, x-ray and/or other ionizing radiation based imaging modalities, exposes the patient to ionizing radiation, which can increase a risk of cancer, radiation poisoning, radiation burns, and/or other ill effects of exposure to ionizing radiation. However, in some instances, one or more of the scans in an imaging examination protocol may be performed, but not used when a radiologist reads the images and dictates the report. Thus, unfortunately, some of the scans may consume time, add cost, and/or expose the patient to ionizing radiation, even though the resulting images are not read by the radiologist and included in the radiologist report.

Generally, a group of imaging experts (e.g., radiologists) at an imaging facility determines which scans and/or reconstructions are included in an imaging examination protocol. This group and/or other group typically reviews the imaging examination protocols, and may add (e.g., where a new imaging technique has emerged) a scan and/or reconstruction. Unfortunately, having one or more individual experts infrequently review the scans is fundamentally limited in that the experts generally do not have sufficient information to make practice-driven or data-driven choices. At least some of the missing information is simply inaccessible as "usefulness" of images is not stored or computed explicitly, but rather inferred from the events produced during routine practice of radiology.

Aspects described herein address the above-referenced problems and others.

In one aspect, a computing device includes a recommender that evaluates at least one of a user interaction with a displayed image of a scan of an imaging examination protocol or information about the scan in an electronically formatted radiology report, and generates a signal including a recommendation to remove the scan only in response to at least one of the user interaction or the radiology report information satisfying predetermined criteria and a output device that visually presents the signal, thereby visually presenting the recommendation.

In another aspect, a method includes evaluating at least one of a user interaction with a displayed image of a scan of an imaging examination protocol or information about the scan in an electronically formatted radiology report and generating a signal including a recommendation to remove the scan only in response to at least one of the user interaction or the radiology report information satisfying predetermined criteria.

In another aspect, a computer readable storage medium is encoded with computer readable instructions, which, when executed by a processor, causes the processor to: evaluate at least one of a user interaction with a displayed image of a scan of an imaging examination protocol or information about the scan in an electronically formatted radiology report, and generate a signal including a recommendation to remove the scan only in response to at least one of the user interaction or the radiology report information satisfying predetermined criteria.

The invention may take form in various components and arrangements of components, and in various steps and arrangements of steps. The drawings are only for purposes of illustrating the preferred embodiments and are not to be construed as limiting the invention.

FIG. 1 schematically illustrates an example imaging system in connection with a computing device implementing an imaging examination protocol update recommender.

Figure 2:
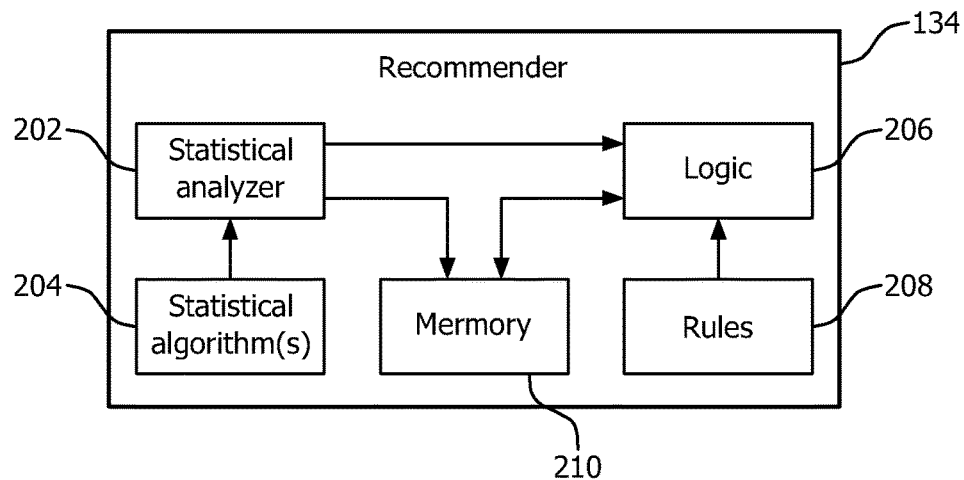

FIG. 2 schematically illustrates an example of the imaging examination protocol update recommender.

Figure 3:
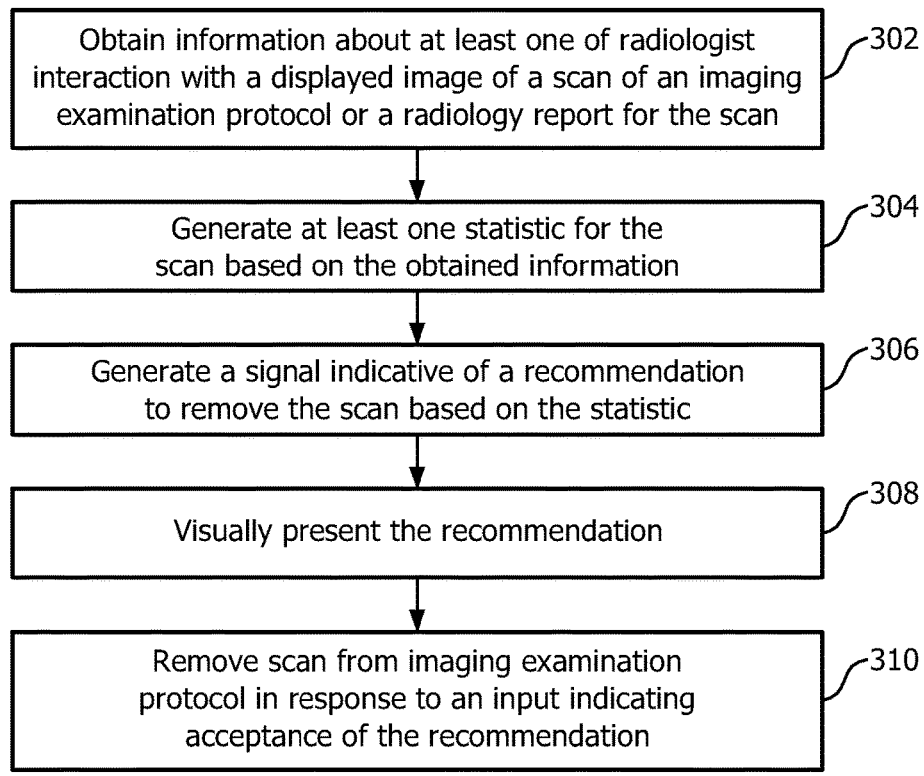

FIG. 3 illustrates an example method for updating an imaging examination protocol.

FIG. 1 schematically illustrates an imaging system 100, which includes a scanner 102, a console 104, a scan protocol bank 106, which includes at least one scan protocol 108, an image processor 110, and an imaging processing algorithm bank 112, which includes at least one imaging processing algorithm 114

The scanner 102 can be any imaging system, including, but not limited to, MRI, CT, x-ray, positron emission tomography (PET), single photon emission tomography (SPECT), ultrasound (US), other imaging scanner and/or a combination thereof such as a so-called hybrid scanner that includes two or more imaging modalities in a single imaging system.

The console 104 includes a general-purpose computing system with a human readable output device such as a monitor and an input device such as a keyboard, mouse, etc. Software resident on the console 104 allows an operator to interact with the scanner 102, including selecting a scan and/or reconstruction corresponding to an imaging examination or scan protocol 108 for a patient to be scanned from the scan protocol bank 106.

The image processor 110 processes the data from the scanner 102 and generates one or more images indicative thereof. The imaging processing algorithm bank 112 includes at least one imaging processing algorithm such as the imaging processing algorithm 114, which is utilized by the image processor 110 to process the data generated by the scanner 102 and produce one or more images.

A data repository 116 includes one or more of a picture archiving and communication system (PACS), a radiology information system (RIS), a hospital information system (HIS), and/or other data storage device. Images generated by the imaging system 100 and/or other imaging system are stored in the data repository 116. Other information stored in the data repository 116 includes, but is not limited to, electronically formatted radiology reports created from images generated by the image processor 110 and/or other device.

An imaging viewing station 118 includes a general-purpose computing system with a human readable output device such as a monitor 119 and an input device such as a keyboard, mouse, etc. Software resident on the imaging viewing station 118 allows the operator to load images from the data repository 116 and/or other device. Loaded images are visually displayed via the monitor 119. The software also includes tools for manipulating displayed images such as pan, zoom, rotate, measure, etc.

The illustrated imaging viewing station 118 also includes an input device sensor 120, a visual sensor 122 and an audio sensor 124. In a variation, the imaging viewing station 118 includes only one or two of the components 120, 122 and 124, and/or one or more other components. Generally, the input device sensor 120 senses key presses, mouse clicks, and/or other inputs corresponding to a loaded image, including an opening of an image, a closing of the image, a length of time the image was opened, a length of time any given input was received while the image was opened, and/or other information about a loaded image.

The visual sensor 122 includes a camera and/or video recorder and tracks eye, hand, head, and/or other movement of the clinician with respect to a loaded image. The tracked position is correlated to the corresponding region of the image. For example, if the clinician is looking at a particular region of the image (e.g., the center), the visual sensor 122 senses where the clinician is looking at in a displayed image and generates a signal indicative thereof. The audio sensor 124 includes a microphone or the like, and records audio from a radiologist (e.g., verbal utterances) about a displayed image. Such audio may be dictation of a report about the image.

A computing device 126 includes at least one processor 128 (e.g., a microprocessor, controller, or the like) which executes computer readable instruction, computer readable storage medium 130 such as physical memory, at least one computer readable instruction 132 such an instruction that implements an imaging examination protocol update recommender ("recommender") 134, and input/output (I/O) 136.

As described in greater detail below, the recommender 134 evaluates an imaging examination protocol and generates a signal indicative of a recommendation as to whether one or more of the scans of the imaging examination protocol should be removed from the imaging examination protocol. In one instance, the signal is generated based on information from at least one of the sensors 120, 122, or 124 and/or the data repository 116, for example, user (i.e., radiologist) interaction with an image of a scan of the imaging examination protocol and/or information about a scan of the imaging examination protocol from an electronically formatted radiology report.

This may facilitate generating, providing and/or maintaining imaging examination protocols that only include scans routinely utilized by radiologists, which may reduce the amount of patient time consumed acquiring data, the amount of technologist time performing scans, the amount of radiologist time reading images, patient and/or insurance cost for the scans, and/or ionizing radiation exposure to the patient (patient dose) when implementing an imaging examination protocol generally by removing and/or not including scans that are not routinely read by radiologists and/or included in radiology reports based on predetermined criteria.

The I/O 136 is configured for receiving information from one or more input devices 138 (e.g., a keyboard, a mouse, and the like), the imaging examination protocol bank 106, the data repository 116, and/or the image viewing station 118, and conveying information to one or more output devices 140 (e.g., a monitor, a printer, portable memory, etc.), the data repository 116. By way of example, the I/O 136 can be used to display the recommendation generated by the recommender 134, accept an input from a radiologist regarding accepting or rejecting the recommendation, etc.

Although the recommender 134 is shown as part of the computing device 126, it is to be appreciated that the recommender 134 or a sub-set of recommender 134 can be part of the console 104, the image viewing station 118, and/or other device.

FIG. 2 schematically illustrates a non-limiting example of the recommender 134.

The illustrated recommender 134 includes a statistical analyzer 202 and one or more statistical algorithms 204. The statistical analyzer 202 employs at least one of the one or more statistical algorithms 204 to compute various statistics based on information from at least one of the data repository 116 and/or one or more of the input device sensor 120, the visual sensor 122, or the audio sensor 124. The statistical analyzer 202 can be invoked to compute the statistics in response to a signal from the image viewing station 118 indicating that an image has been opened (and loaded in the image viewing station 118), the data repository indicating a report has been stored therein, and/or otherwise. The computed statistics can be stored in local memory 210, the data repository 116, and/or elsewhere.

In this example, one statistical algorithm 204 instructs the statistical analyzer 202 to count a number of times an image of a scan of an imaging examination protocol of a patient study is opened, or loaded in the image viewing station 118. For instance, where the study includes an imaging examination protocol with N different scans and the patient is scanned N times according to the N different scans, generating N sets of images, the statistical algorithm 204 causes the statistical analyzer 202 to increment a count value, via a counter or the like, for an image and/or the corresponding scan each time that image is opened. From this data, the statistical analyzer 202 can determine a statistic indicative of a number of times a scan of the imaging examination protocol is opened as a function of a number of times any of the scans of the imaging examination protocol is opened. This can also be performed on a basis of an image of a scan.

Another statistical algorithm 204 instructs the statistical analyzer 202 to determine a length of time an image of a scan of an imaging examination protocol of a patient study is opened, or loaded in the image viewing station 118. For instance, continuing with the above example, for each image opened, the statistical analyzer 202 measures, via a timer or the like, a time duration from the opening of the image to the closing of the image. From this data, the statistical analyzer 202 can determine a statistic indicative of the amount of time an image of a particular scan is opened as a function of a time an image of any of the scans of the imaging examination protocol is opened. The statistical analyzer 202 can also measure the time between openings of an image of a scan of an imaging examination protocol. From this data, the statistical analyzer 202 can determine a statistic indicative of a frequency in which an image of the scan is opened as a function of a time when an image of any of the scans of the imaging examination protocol is opened.

Another statistical algorithm 204 instructs the statistical analyzer 202 to determine a number of input device (e.g., graphical pointer and/or keyboard) operations in connection with an image of a scan of an imaging examination protocol of a patient study that is opened, or loaded in the image viewing station 118. For instance, continuing with the above example, the radiologist viewing an image of a scan of an imaging examination protocol may move a pointer around the image and/or click on a region of the image with the pointer, press one or more keyboard keys, etc., and the statistical analyzer 202 counts such events and/or measures a length of the such events. From this data, the statistical analyzer 202 can determine one or more statistics indicative of a frequency and/or duration of such events. Where the pointer is used to invoke a manipulation to the image (e.g., pan, zoom, rotate, segment, measurement, etc.), the statistical analyzer 202 can determine a statistic indicative of a number of total manipulations, a frequency of manipulations, a time length (e.g., average, minimum, maximum, etc.) of the manipulations, etc.

Another statistical algorithm 204 instructs the statistical analyzer 202 to determine a number of times a scan of an imaging examination protocol is included in one or more sections (e.g., "Findings", "Conclusions", etc.) of a radiology report. Another statistical algorithm 204 instructs the statistical analyzer 202 to determine a number of times a term with a strong correlation to a scan of an imaging examination protocol is included in one or more sections of a radiology report. This may be accomplished through a combination of known and/or proprietary approaches of text searching with a database of imaging terms, synonyms, and/or related terms. For example, in the case of a specific type of MR pulse sequence, the series itself maybe titled "T2 FLAIR." A database of equivalent terms "T2-weighted FLAIR," "T2 Fluid Attenuated Inversion Recovery," etc. may be included, as well as terms with a correlation to the scans such as "T2 hyperintensity," "FLAIR abnormality," "edema seen on T2," "T2 abnormality," etc.

In a variation, a numerical strength of association index may be included for each term such that weaker correlations (e.g. "hyperintensity" for series types "T2" and "T1") are scored differently than stronger correlations (e.g., "contrast enhancement" for "Post-Gd T1"). This association index may be computed in any number of ways and pre-defined. In one instance, the strength of association is computed from the co-occurrence of dictated words with the image shown on the screen, calculated over a large series of examination reports. In another instance, the strength of association may be based on co-occurrence of words and phrases with the names of the series, computed over a large series of examination reports.

In another variation, the text search may be performed with the additional use of known methods of natural language processing, such as stemming (e.g. replacing "hyperintensity" with "hyperintens*" such that "hyperintense" is also recorded as a match), spell checking, removal of stop words ("the", "is", "at", etc) and checking for word transpositions. In another variation, the text search may be limited to certain parts of the report, such as the findings or impressions. Excluding the "procedure" section, if any, may exclude spurious references to series that occur when a list of performed scans is copied directly into the report text. In another variation, if the report is dictated through voice recognition software, the statistics may be extended to include the number of words (total or a pre-defined subset) dictated while each image is on the screen, i.e. an image is more likely to be "useful" if it is on screen while the radiologist is dictating.

In another variation, a record is kept of the correlation (co-occurrence) of a scan with a clinical finding in the report or the clinical indication in the imaging order. Thus, all of the foregoing statistics can be split further into the statistics in the presence of a pathology or the absence of a pathology. For example, it may be generally true that on average, when a basic brain MR examination is performed the diffusion image is not used or reported upon, but when we consider only those patients with a suspicion of brain tumor, then the diffusion image is almost always used or reported upon. As an illustrative example, consider the report fragment, where the references to the different imaging series are indicated in bold/underlining:

There are nonspecific foci of increased T2 signal scattered throughout the periventricular white matter in a symmetrical distribution. These do not show any enhancement. There are a few bright foci of signal intensity on the diffusion-weighted imaging in the same location; however, these remain bright on the ADC map and are therefore consistent with T2 shine through rather than acute ischemia. These findings are most consistent with chronic small vessel ischemic changes.

There is a dural base mass in the skull base. The mass is at the anterior aspect of the foramen magnum. The lesion is moderately hyperintense on T2 and hypointense on T1. The mass has a uniform enhancement pattern and is consistent with a meningioma.

Note that references in a report generally cannot be considered definitive as to whether or not a scan is considered useful, but when aggregated over a large number of examinations and in combination with other factors, may be indicative of usefulness of a series.

The statistical analyzer 202 computes the above and/or other statistics for a plurality of imaging examination protocols. The statistics can be sorted and stored on a patient study-by-patient study basis. Within each imaging examination protocol type, the statistics can be sorted and stored on a scan-by-scan basis, aggregated across many imaging examination protocols, etc. In one non-limiting instance, the statistics can be stored in the form of a table, for example, as shown in Table 1 below for a MRI Brain Tumor imaging examination protocol.

TABLE 1

MRI Brain Tumor imaging examination protocol.

| Scan | Type | Fraction of times opened | Fraction of times reported |
| --- | --- | --- | --- |
| 1 | Sag T1 | 0.20 | 0.01 |
| 2 | Ax T1 | 0.75 | 0.11 |

TABLE 1-continued

MRI Brain Tumor imaging examination protocol.

| Scan | Type | Fraction of times opened | Fraction of times reported |
|------|---------|--------------------------|----------------------------|
| 3 | T2 TSE | 0.98 | 0.41 |
| 4 | T2 FLAIR | 1.00 | 0.83 |
| 5 | Cor T2 | 0.21 | 0.07 |

In this example, the "Sag T1" was opened 20% of the time it was acquired and was referenced in the reports 1% of the time it was acquired. The "Ax T1" was opened 75% of the time it was acquired and was referenced in the reports 11% of the time it was acquired. The "T2 TSE" was opened 98%> of the time it was acquired and was referenced in the reports 41% of the time it was acquired. The "T2 FLAIR" was opened 100% of the time it was acquired and was referenced in the reports 83% of the time it was acquired. The "Cor T2" scan was opened 21% of the time it was acquired and was referenced in the reports 7% of the time it was acquired.

Again, the above table is provided for explanatory purposes and is not limiting. As such, one or more other fields may be included and/or one or more of the included fields can be omitted. For example, the analysis may include aggregating all the data for a particular imaging examination protocol or, the data for this imaging examination protocol may be separated based on refinement criteria such as, but not limited to, clinical indication, demographics, imaging facility, interpreting radiologist, etc. In this instance, the statistics for the same imaging examination protocol may include sub-sets of the same statistics with different values that are tailored toward the refinement criteria.

It is to be appreciated that the interaction information from the image viewing station 118 and/or the radiology reports from the data repository 116 can be used alone or in combination. Furthermore, analysis of the radiology reports may be performed off-line in a retrospective fashion, for example, through analysis of previously written radiology reports.

The recommender 134 further includes logic 206 that generates a signal indicative of a recommendation as to whether to modify the scans in the imaging examination protocol based on the above-noted and/or other statistics. In the illustrated embodiment, the logic 206 determines the recommendation based on the statistics and one or more rules 208. For example, one of the rules 208 may result in the logic 206 generating a recommendation that one or more of the scans of an imaging examination protocol should be removed.

By way of non-limiting example, in one instance, one of the rules 208 includes a threshold value and instructs the logic 206 to compare one or more of the statistics (e.g., individually, or an average, weighted average or other combination of multiple statistics) with the threshold value. The one of the rules 208 further instructs the logic 206 what to do depending on whether the one or more of the statistics satisfies the threshold value. For instance, if the one or more of the statistics for a particular scan of the imaging examination protocol satisfies the threshold value, the logic 206 generates a signal indicating the recommendation of removing the scan from the imaging examination protocol. Where the above-noted refinement criterion is employed, the signal may include different recommendations depending on the imaging facility, the clinical indications, the radiologist, etc.

The recommendation can be visually presented through the output device 140, the console 104, the image viewing station 118, and/or other device. The value of the statistic and the threshold value can also be displayed. If the clinician accepts the recommendation, the logic 206 changes the imaging examination protocol accordingly, and the updated imaging examination protocol can be conveyed to the data repository 116, and/or other device. The clinician can accept the recommendation using the input device 138, the console 104, the image viewing station 118, and/or otherwise, including a web based application, a cell or smartphone application, a text message, an email, a voice command, etc.

In a variation, one of the rules 208 causes the logic 206 to order the scans of an imaging examination protocol in a list that is visually presented via the output device 140 and/or other device based on the statistics. For example, in one instance the scans are ordered such that candidates for removal are located at the bottom of the list. This may facilitate locating scans to remove from the imaging examination protocol during imaging examination protocol review, skipping scans when implementing an imaging examination protocol for a patient, etc.

In another variation, one of the rules 208 causes the logic 206 to exclude some of the scans of an imaging examination protocol from removal consideration. For example, one or more of the scans of an imaging examination protocol may be acquired regularly as part of a clinical trial but not reviewed by radiologists, and thus receive low "usefulness" statistics. In one instance, such scans should not be considered as candidates for removal. In another example, a CT reconstruction that is needed for in-surgery use may similarly not be opened by a reading radiologist but should be performed and thus also not considered a candidate for removal, regardless of the statistics.

In another variation, one of the rules 208 may include a subdivision into clinical categories as described herein. In yet another variation, one of the rules 208 may include the numerical strength of correlation described herein.

The above described an example in which the recommender 134 recommends a scan(s) to be removed from an imaging examination protocol. In another instance, the recommender 134 additionally or alternatively recommends adding a scan(s) to the imaging examination protocol.

For example, the recommender 134 may determine that at least one of the scans of an imaging examination protocol has a high degree of correlation with another scan that is not presently included in the imaging examination protocol. That is, when the subject scan is performed, the other scan is also performed a predetermined amount of the time with other imaging examination protocols. This may be determined based on a correlation value determined from an analysis of multiple other imaging examination protocols, a scan
correlation value provided to the recommender 134, etc. In this case, the recommender 134 generates a signal recommending adding the scan, and this information is visually displayed and can be accepted or rejected as described herein.

In yet another instance, the scan correlation information associated with an imaging examination protocol under evaluation is used to recommend removing and/or adding a scan(s) to another imaging examination protocol. For example, two scans are performed for a predetermined number of imaging examination protocols and only one of those scan is included in a particular imaging examination protocol, the recommender 134 may generate a signal to indicate that the other scan should be added to the particular imaging examination protocol.

FIG. 3 illustrate an example method for updating an imaging examination protocol.

It is to be appreciated that the ordering of the acts in the methods described herein is not limiting. As such, other orderings are contemplated herein. In addition, one or more acts may be omitted and/or one or more additional acts may be included.

At 302, information about at least one of radiologist interaction with a displayed image of a scan of an imaging examination protocol of a patient study or information from a radiology report for the scan is obtained.

At 304, at least one statistic is generated for at least one scan of the imaging examination protocol based on the obtained information, for example, as described herein and/or otherwise.

At 306, a signal indicative of a recommendation to remove at least one scan of the imaging examination protocol based on the at least one statistic is generated, as described herein.

At 308, the recommendation is visually presented.

At 310, the at least one scan is removed from the imaging examination protocol only in response to receiving an input indicating radiologist acceptance of the recommendation. In another instance, the removal of the scan can be automatically performed. Of course, a radiologist and/or other authorized personnel can override the removal.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A system, comprising:
   a data repository configured to store a plurality of images;
   a viewing station comprising:
      a display monitor configured to visually present a displayed image, wherein the displayed image is selected from the plurality of images and corresponds to a scan, wherein the scan is within an electronically stored examination protocol;
      at least one sensor configured evaluate a plurality of radiologist interactions reading the displayed image and to generate an output based on the evaluated radiologist interaction with the displayed image, wherein the at least one sensor is selected from the group consisting of:
         a visual sensor configured to track movement of the radiologist viewing the displayed image;
         an audio sensor configured to record audio uttered by the radiologist; and
         an input device sensor configured to sense inputs corresponding to the displayed image; and
      a computing device comprising:
         a processor; and
         a memory encoded with computer readable instructions which when executed by the processor cause the processor to:
            determine at least one statistic based on the generated output; and
            in response to determining the at least one statistic satisfies a predetermined threshold, remove the scan that corresponds to the displayed image from the examination protocol.

2. The system of claim 1, wherein the processor is further configured to:
   determine the at least one statistic about the scan relative to at least one other scan of the imaging examination protocol; and
   remove the scan based on the at least one statistic and at least one rule, wherein the at least one rule determines satisfaction of the predetermined threshold according to the at least one statistic.

3. The system of claim 2, wherein the at least one statistic is based on at least one radiologist interaction selected from a group comprising of: a number of times the image is opened as a function of a number of times an image of any of the scans of the imaging examination protocol is opened, a length of time the image is opened as a function of a length of time an image of any of the scans of the imaging examination protocol is opened, a length of time between openings of the image, a frequency of an input device event with respect to the displayed image, and a time duration of the input device event with respect to the displayed image.

4. The system of claim 2, wherein the at least one statistic is based on at least one radiologist interaction selected from a group consisting of: a frequency of an image manipulation of the displayed image, a time duration of an image manipulation of the displayed image, and a total number of image manipulations of the displayed image.

5. The system of claim 2, wherein the at least one statistic is visually presented and delineated based on at least one selected from a group consisting of: an imaging examination protocol, a patient study, and a scan.

6. The system of claim 2, wherein the at least one statistic is delineated based on at least one selected from a group consisting of: a clinical indication, a patient demographic, an imaging facility, and an interpreting radiologist.

7. The system of claim 2, wherein the scan is presented in an ordered list of scans of the same imaging examination protocol based on the at least one statistic.

8. The system of claim 1, wherein at least one scan of the same imaging examination protocol is excluded from the evaluation.

9. The system of claim 2, wherein the predetermined criteria is a threshold value, the at least one statistic is compared against the threshold value, and the signal including the recommendation to remove the scan from the same imaging examination protocol is generated in response to the statistic being less than the threshold value;
   wherein the recommender updates the same imaging examination protocol in a scan protocol bank.

10. The system of claim 1, wherein the plurality of radiologist interactions reading the displayed image comprises at least one input from a sensor selected from a group consisting of: a visual sensor input tracking of an eye of a radiologist with respect to the displayed image, and an audio sensor input of verbal utterance of the radiologist while the displayed image is displayed; and
   wherein the recommender generates the signal based the evaluation of the input from the sensor.

11. The system of claim 2, wherein the signal further includes at least one of a recommendation to add a scan to the same imaging examination protocol or a recommendation to add a scan to another imaging examination protocol.

12. A method, comprising:
- displaying an image that corresponds to a scan, wherein the scan is within an electronically stored examination protocol;
- determining a radiologist interaction with the displayed image, wherein the radiologist interaction is determined by at least one sensor selected from the group consisting of:
  - a visual sensor configured to track movement of a radiologist viewing the displayed image;
  - an audio sensor configured to record audio uttered by the radiologist; and
  - an input device sensor configured to sense inputs corresponding to the displayed image;
- generating an output based on the radiologist interaction with the displayed image;
- determining at least one statistic based on the generated output; and
- in response to determining the at least one statistic satisfies a predetermined threshold, removing the scan that correspond to the displayed image from the examination protocol.

13. A non-transitory computer readable storage medium encoded with computer readable instructions, which, when executed by a processor, causes the processor to:
- displaying an image that corresponds to a scan, wherein the scan is within an electronically stored examination protocol;
- determine a radiologist interaction with the displayed image, wherein the radiologist interaction is determined by at least one sensor selected from the group consisting of:
  - a visual sensor configured to track movement of a radiologist viewing the displayed image;
  - an audio sensor configured to record audio uttered by the radiologist; and
  - an input device sensor configured to sense inputs corresponding to the displayed image;
- generate an output based on the radiologist interaction with the displayed image;
- determine at least one statistic based on the generated output; and
- in response to determining the at least one statistic satisfies a predetermined threshold, remove the scan that correspond to the displayed image from the examination protocol.

14. The method according to claim 12, wherein the at least one statistic is relative to a radiologist interaction with at least one other scan of the same imaging examination protocol; and
- wherein the removal is based on the at least one statistic and at least one rule, wherein the at least one rule determines satisfaction of the predetermined threshold according to a the at least one statistic.

15. The method according to claim 14, wherein the at least one statistic is based on the information about a scan selected from a group consisting of: a total number of times the scan is included in one of the radiology reports, a total number of times a term with a strong correlation to the scan of the same imaging examination protocol is included in one of the radiology reports, and a correlation of a displayed image read by a radiologist with a clinical finding in one of the radiology reports.

16. The non-transitory computer readable storage medium according to claim 13, wherein the at least one statistic is based on the radiologist interaction selected from a group consisting of: a number of times the displayed image is opened as a function of a number of times an image of any scan of the same imaging examination protocol is opened for reading, a length of time the displayed image is open as a function of a length of time an image of any scan of the same imaging examination protocol is open for reading, a length of time between openings of any image of the same imaging examination protocol for reading, a frequency of an input device event with respect to the displayed image, a time duration of the input device event with respect to the displayed image, a frequency of an image manipulation of the displayed image, a time duration of an image manipulation of the displayed image for reading, and a total number of image manipulations of the displayed image for reading.

17. The non-transitory computer readable storage medium according to claim 13, wherein the at least one statistic is based on the information about the scan selected from a group consisting of: a total number of times the scan is included in one of the radiology reports for the same imaging examination protocol, a total number of times a term with a strong correlation to the scan of the same imaging examination protocol is included in one of the radiology reports, and a correlation of the displayed image with a clinical finding in one the radiology reports.

18. The system of claim 1, wherein the visual sensor tracks eye movement of the radiologist with respect to the displayed image as the racked movement, and the tracked movement is correlated to a region of the displayed image.

* * * * *